United States Patent
Barron et al.

(10) Patent No.: US 10,207,095 B2
(45) Date of Patent: Feb. 19, 2019

(54) FAST CLEAR PORT

(75) Inventors: William R. Barron, Riverton, UT (US); Terri C. Bateman, American Fork, UT (US); Jared M. Crosby, Provo, UT (US); Aaron M. Krimme, Provo, UT (US); Jonathan Oldham, Orem, UT (US); Jorge L. Saltos, Provo, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 2634 days.

(21) Appl. No.: 11/300,192

(22) Filed: Dec. 14, 2005

(65) Prior Publication Data

US 2006/0178648 A1    Aug. 10, 2006

Related U.S. Application Data

(60) Provisional application No. 60/635,818, filed on Dec. 14, 2004.

(51) Int. Cl.
*A61M 39/02* (2006.01)
*A61M 39/04* (2006.01)

(52) U.S. Cl.
CPC ......... *A61M 39/0208* (2013.01); *A61M 39/04* (2013.01); *A61M 2039/0211* (2013.01); *A61M 2039/0214* (2013.01)

(58) Field of Classification Search
CPC .............. A61M 39/0208; A61M 25/02; A61M 2025/0008; A61M 2025/0213; A61M 2025/0273; A61M 2025/0681; A61M 2025/0246; A61M 2039/0211; A61M 2039/1072; A61M 39/10; A61M 2039/0232

USPC ............ 604/93.01, 116, 173–175, 244, 256, 604/288.01–288.04, 908

See application file for complete search history.

(56) References Cited

U.S. PATENT DOCUMENTS

| | | | |
|---|---|---|---|
| 4,190,040 A * | 2/1980 | Schulte ...................... | A61F 2/12 128/899 |
| 4,543,088 A * | 9/1985 | Bootman .......... | A61M 39/0208 604/175 |
| 4,581,012 A * | 4/1986 | Brown et al. .................... | 604/43 |
| 4,634,427 A * | 1/1987 | Hannula ............. | A61M 5/1428 604/185 |
| 4,692,146 A * | 9/1987 | Hilger ................ | A61M 39/0208 604/173 |
| 4,695,273 A * | 9/1987 | Brown .......................... | 604/173 |

(Continued)

FOREIGN PATENT DOCUMENTS

WO    2006066023 A2    6/2006

OTHER PUBLICATIONS

PCT/US2005/045470 filed Dec. 14, 2005 Preliminary Report on Patentability dated Jun. 19, 2007.

(Continued)

*Primary Examiner* — Bhisma Mehta
*Assistant Examiner* — Matthew A Engel
(74) *Attorney, Agent, or Firm* — Rutan & Tucker, LLP

(57) ABSTRACT

Described herein are implantable ports including a housing with a fluid receptacle, a port stem in fluid communication with the fluid receptacle, and a septum covering the fluid receptacle. The ports may be configured to reduce the priming volume by including a plurality of fluid-locked chambers and/or one or more base mats. The ports may also include a hydrophobic coating on one or more surfaces thereof.

17 Claims, 4 Drawing Sheets

(56) References Cited

U.S. PATENT DOCUMENTS

| | | | | |
|---|---|---|---|---|
| 4,767,410 A * | 8/1988 | Moden et al. | ................ | 604/175 |
| 4,772,270 A * | 9/1988 | Wiita et al. | ................... | 604/175 |
| 4,832,054 A * | 5/1989 | Bark | ................. | A61M 39/0208 |
| | | | | 128/899 |
| 4,892,518 A * | 1/1990 | Cupp | ................ | A61M 39/0208 |
| | | | | 137/855 |
| 4,929,236 A * | 5/1990 | Sampson | .............. | A61M 39/12 |
| | | | | 128/912 |
| 4,963,133 A | 10/1990 | Whipple | | |
| 4,969,873 A * | 11/1990 | Steinbach | ......... | A61M 5/14276 |
| | | | | 128/DIG. 12 |
| 5,045,060 A | 9/1991 | Melskey et al. | | |
| 5,084,015 A * | 1/1992 | Moriuchi | .......... | A61M 39/0208 |
| | | | | 604/185 |
| 5,108,377 A * | 4/1992 | Cone | ..................... | A61M 5/165 |
| | | | | 604/175 |
| 5,129,891 A | 7/1992 | Young | | |
| 5,137,529 A * | 8/1992 | Watson | ............. | A61M 39/0208 |
| | | | | 128/DIG. 12 |
| 5,167,638 A * | 12/1992 | Felix et al. | .................. | 604/175 |
| 5,306,255 A * | 4/1994 | Haindl | ............ | A61M 39/0208 |
| | | | | 604/175 |
| 5,312,337 A | 5/1994 | Flaherty et al. | | |
| 5,318,545 A | 6/1994 | Tucker | | |
| 5,360,407 A * | 11/1994 | Leonard | ............ | A61M 39/0208 |
| | | | | 604/116 |
| 5,399,168 A * | 3/1995 | Wadsworth, Jr. | ........................... | |
| | | | | A61M 39/0208 |
| | | | | 604/175 |
| 5,476,460 A | 12/1995 | Montalvo | | |
| 5,562,618 A * | 10/1996 | Cai | ................... | A61M 39/0208 |
| | | | | 604/175 |
| 5,613,945 A * | 3/1997 | Cai | ................... | A61M 39/0208 |
| | | | | 604/116 |
| 5,695,490 A * | 12/1997 | Flaherty | ............ | A61M 39/0208 |
| | | | | 128/DIG. 12 |
| 5,792,104 A * | 8/1998 | Speckman | ........ | A61M 39/0208 |
| | | | | 604/175 |
| 5,833,654 A * | 11/1998 | Powers | ............. | A61M 39/0208 |
| | | | | 604/175 |
| 5,931,801 A * | 8/1999 | Burbank | ............ | A61M 1/3653 |
| | | | | 604/4.01 |
| 5,951,512 A * | 9/1999 | Dalton | ............. | A61M 39/0208 |
| | | | | 604/175 |
| 6,056,717 A * | 5/2000 | Finch et al. | ............... | 604/93.01 |
| 6,086,555 A * | 7/2000 | Eliasen et al. | ............. | 604/93.01 |
| 6,113,572 A | 9/2000 | Gailey | | |
| 6,213,973 B1 | 4/2001 | Eliasen et al. | | |
| 6,287,293 B1 | 9/2001 | Jones et al. | | |
| 6,478,783 B1 | 11/2002 | Moorehead | | |
| 6,537,242 B1 * | 3/2003 | Palmer | ............................ | 604/22 |
| 7,811,266 B2 * | 10/2010 | Eliasen | ............. | A61M 39/0208 |
| | | | | 604/288.01 |
| 8,025,639 B2 * | 9/2011 | Powers | ............. | A61M 39/0208 |
| | | | | 604/131 |
| 2003/0028173 A1 | 2/2003 | Forsberg | | |
| 2005/0171502 A1 * | 8/2005 | Daly et al. | .................... | 604/502 |
| 2006/0084929 A1 | 4/2006 | Eliasen | | |
| 2007/0073250 A1 | 3/2007 | Schneiter | | |
| 2007/0078391 A1 | 4/2007 | Wortley et al. | | |
| 2007/0078416 A1 | 4/2007 | Eliasen | | |
| 2009/0118683 A1 * | 5/2009 | Hanson et al. | .......... | 604/288.01 |

OTHER PUBLICATIONS

PCT/US2005/045470 filed Dec. 14, 2005 Search Report dated Nov. 30, 2006.

PCT/US2005/045470 filed Dec. 14, 2005 Written Opinion dated Nov. 30, 2006.

\* cited by examiner

*FIG. 7A*
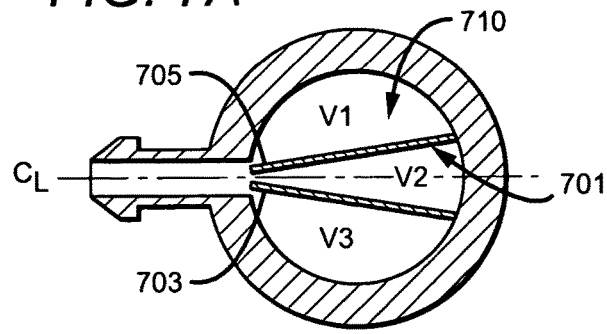
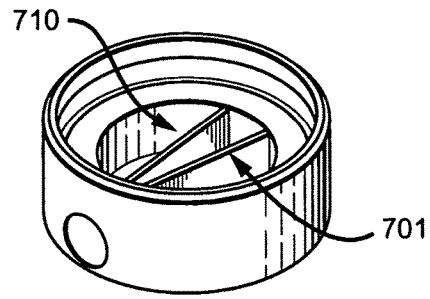
*FIG. 7B*
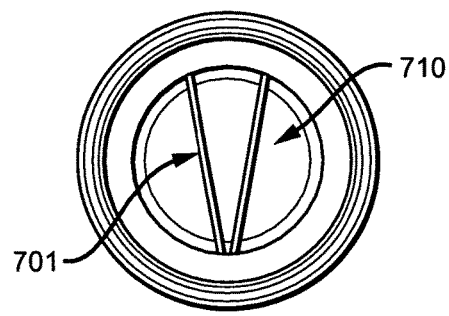
*FIG. 7C*
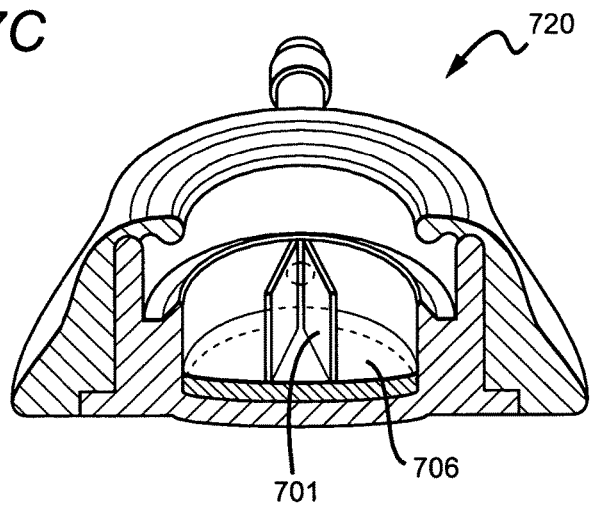
*FIG. 7D*
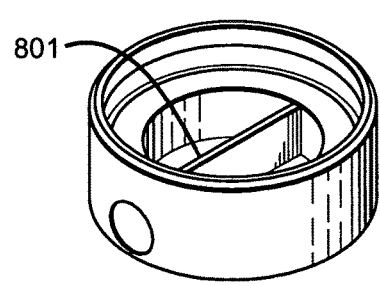
*FIG. 8*

FAST CLEAR PORT

CROSS-REFERENCE TO RELATED APPLICATIONS

This application claims the benefit under 35 U.S.C. § 119(e), to U.S. Provisional Application No. 60/635,818, filed Dec. 14, 2004, which is incorporated by reference into this application as if fully set forth herein.

BACKGROUND OF THE INVENTION

A variety of subcutaneously implantable access ports have been utilized by physicians to deliver fluids to, or withdraw fluids from, the bloodstream or other subcutaneous cavities inside a patient. Such vascular access ports generally include a needle-impenetrable housing enclosing a fluid reservoir that is sealed by a needle penetrable septum. The access port also includes a port stem that projects from the housing and has a fluid passageway that communicates with the fluid reservoir. The port stem can be used to couple a catheter to the housing.

Typically, an access port may be attached to a catheter (e.g., via the port stem) after the catheter has been inserted within a subject. The access port is then implanted into an appropriate region of the subject's body so that the distal end of the catheter is disposed at a predetermined location where a therapeutic agent is to be delivered from the access port. Once the vascular access port is implanted, a needle attached to a syringe can selectively access the reservoir of the access port by penetrating the subject's skin overlaying the access port and enter the septum of the access port. The needle and syringe can then deliver fluids (including fluids containing medication or other therapeutics) to the target site. The fluids travel through the reservoir, port stem, and catheter, and are released from the distal end of the catheter. Alternatively, a syringe can be used to aspirate and withdraw bodily fluids from the region near the distal end of the catheter.

Fluid (e.g., medication) may be dispensed from the fluid reservoir of the access port by means of a non-coring needle, inserted through the penetrable septum. For example, this fluid may be applied from the distal end of the catheter to an entry point into the venous system of the body of the patient. Blood may also be withdrawn (e.g., for sampling) from the body of the patient through an access port by applying negative pressure in the fluid cavity, drawing blood through the catheter, into the fluid cavity, and then out of the body of the patient through the needle. To prevent clotting, the withdrawal route may be flushed with a saline solution or heparin using a non-coring needle injected into the access port in the same manner as if a medication were being infused. Both intermittent and continual injections of medication may be dispensed by the access port. Continual access may involve the use of a non-coring needle attached to an ambulatory-type pump or gravity feed bag suspended above the patient. The ambulatory-type pump or the gravity feed bag continually delivers the medication or fluid through the needle to the fluid cavity in the access port and from there through the catheter to the entry point into the venous system.

Examples of access ports are described in U.S. Pat. No. 4,772,270, titled "INSEPARABLE PORT/CATHETER TUBE ASSEMBLY AND METHODS" issued to Wiita et al., dated Sep. 20, 1988; U.S. Pat. No. 4,963,133, titled "CATHETER ATTACHMENT SYSTEM" issued to Whipple, dated Oct. 16, 1990; U.S. Pat. No. 5,045,060, titled "IMPLANTABLE INFUSION DEVICE" issued to Melsky et al., dated Sep. 3, 1991; U.S. Pat. No. 5,129,891, titled "CATHETER ATTACHMENT DEVICE" issued to Young, dated Jul. 14, 1992; U.S. Pat. No. 5,137,529, titled "INJECTION PORT" issued to Watson et al., dated Aug. 11, 1992; U.S. Pat. No. 5,312,337, titled "CATHETER ATTACHMENT DEVICE" issued to Flaherty et al., dated May 17, 1994; U.S. Pat. No. 5,360,407, titled "IMPLANTABLE DUAL ACCESS PORT WITH TACTILE RIDGE FOR POSITION SENSING" issued to Leonard, dated Nov. 1, 1994; U.S. Pat. No. 5,399,168, titled "IMPLANTABLE PLURAL FLUID CAVITY PORT" issued to Wadsworth, Jr. et al., dated Mar. 21, 1995; U.S. Pat. No. 5,833,654, titled "LONGITUDINALLY ALIGNED DUAL RESERVOIR ACCESS PORT" issued to Powers et al., dated Nov. 10, 1998; U.S. Pat. No. 6,113,572, titled "MULTIPLE-TYPE CATHETER CONNECTION SYSTEMS" issued to Gailey et al., dated Sep. 5, 2000; U.S. Pat. No. 6,213,973, titled "VASCULAR ACCESS PORT WITH ELONGATED SEPTUM" issued to Eliasen et al., dated Apr. 10, 2001; and U.S. Pat. No. 6,287,293, titled "METHOD AND APPARATUS FOR LOCATING THE INJECTION POINT OF AN IMPLANTED MEDICAL DEVICE" issued to Jones et al., dated Sep. 11, 2001, each of which is incorporated herein by reference in its entirety.

In certain circumstances, it may be desirable to reduce the priming volume of an access port to enhance the clearance of fluid (including medications) from the access port. The "priming volume" of an access port is defined herein as the volume of fluid contained within the port and port stem (and may include the fluid within an attached catheter). Reducing the priming volume may decrease the amount of fluid required to flush fluid from the access port, also referred to as clearing the access port. However, applicants have recognized that there is a tradeoff between the size and ease of use of the access catheter and the priming volume. In particular, an access port must be deep enough for the needle to penetrate the septum such that the opening in the needle tip is within the reservoir to allow fluid to pass into and out of the needle. Thus, most commonly available access ports are relatively large in size (e.g., have a large housing and fluid reservoir) so that they are easy to locate and inject into; however, as mentioned, the large size may contribute to a larger than optimal priming volume therein.

In certain circumstances, applicants have recognized that it can be desirable to provide access ports with geometries and configurations that assist in reducing the priming volume. Such access ports may be referred to herein as "fast clear ports." Thus, described herein are fast clear ports, systems including fast clear ports, methods of using fast clear ports, and methods of manufacturing fast clear ports.

BRIEF SUMMARY OF THE INVENTION

Accordingly, described herein are fast clear ports configured to rapidly clear fluid. In one embodiment, a fast clear port includes a multi-chamber implantable vascular access port having a housing with a divided fluid receptacle (divided into a plurality of chambers), a port stem in fluid connection with the chambers of the receptacle, and a septum configured to cover the fluid receptacle. The port stem may be configured to couple to a catheter. Multi-chamber access ports may have any number of chambers and may include a number of configurations. In one embodiment, a single fluid receptacle may be divided into more than one chamber into which fluid may be applied or withdrawn by a needle inserted through a port septum. For example, the single fluid receptacle of the access port may be divided up into two, three, or more chambers. Generally, a divided single fluid receptacle is covered by a single septum that covers all of the chambers. A needle may be inserted through the septum into any of the adjacent chambers of the receptacle.

In some variations, the fluid receptacle of the access port is divided up into a plurality of fluid-locked chambers. As used herein, the term "fluid-locked" means that injection (or withdrawal) of fluid from one of the chambers does not substantially change the fluid within the other chambers (although some fluid may be exchanged at the interface between the chambers by diffusion or due to turbulence); instead, the majority of fluid is exchanged between the chamber and the port stem, which may be connected to a catheter implanted into a subject's vasculature. As described further below, the fluid-locked chambers are configured so that as fluids are infused or aspirated from the system, only fluid in the accessed chamber are exchanged, as differential fluid pressures are not created to cause fluid to flow in the other chamber(s). Thus, there is no substantial fluid flow between the chamber into which the fluid is applied and the other chamber(s). In one embodiment, the plurality of fluid-locked chambers may divide the fluid receptacle into approximately equivalent volumes.

In one embodiment, the fluid-locked chambers are formed by at least one insert. The insert may be one or more pieces of formed material (e.g., metal, plastic, etc.) that is shaped to create barriers separating the receptacle into multiple chambers when inserted into the fluid receptacle of the access port. The insert may be a separate insert (e.g., formed separately form the rest of the housing) or it may be integral to the housing of the access port (e.g., formed as part of the rest of the housing). The insert may include an opening or gap to allow fluid to flow between each chamber of the fluid receptacle and the port stem. In some variations, the opening is oriented along the centerline of the port stem. The insert may be any appropriate shape and may have an open "top" over which the septum fits so that a needle can access the chambers. For example, the insert may be configured as a round, linear, or pie-shaped insert.

In another embodiment, a fast clear port may include a base mat disposed within the fluid receptacle. In general, the base mat may be positioned on the base of the fluid receptacle and can reduce the fluid volume within the receptacle (or chambers of the receptacle in multi-chamber access ports), while allowing the needle (e.g., the sharp or beveled tip of the needle) to penetrate into the fluid mat so that opening into the lumen of the needle can be properly positioned within the receptacle. Thus, the tip of the needle may penetrate into the base mat (and eventually contact the bottom of the reservoir in the housing), allowing the opening in the needle to access the fluid receptacle (or one of the chambers in a divided fluid receptacle). The base mat may be made of any appropriate material that permits the penetration of a needle. For example, the base mat may comprise a silicone mat. Materials that are not easily "cored" by a needle (e.g., elastomeric materials) may be particularly useful.

In one embodiment, a multi-chamber implantable vascular access port includes a housing having a divided fluid receptacle (that is divided into a plurality of chambers), a base mat disposed within the divided fluid receptacle, a port stem in fluid connection with each chamber of the receptacle, and a septum configured to cover the chamber. The port stem is configured to couple to a catheter. In some variations, a cover may be included that has a window or opening exposing the septum. The cover may attach to the housing.

In some variations, the fluid-contacting surfaces within the receptacle of an access port are hydrophobic. These fluid-contacting surfaces (e.g., the walls, floor, etc.) may be made of, layered, or coated with a hydrophobic material, including highly hydrophobic materials. For example, the fluid-contacting surfaces may comprise polytetrafluoroethylene (PTFE). Hydrophobic (or lubricious) surfaces may also enhance fluid clearance from the access port.

In one embodiment, an implantable port includes a housing including a fluid receptacle divided into two or more chambers, a port stem in fluid communication with the fluid receptacle, and a septum configured to cover the fluid receptacle such that the chambers are fluid-locked. In another embodiment, an implantable port includes a housing including a fluid receptacle divided into a plurality of chambers, a base mat disposed within the fluid receptacle, a port stem in fluid communication with each of the chambers, and a septum configured to cover the fluid receptacle.

Also described herein are methods of manufacturing an implantable vascular access port having a divided fluid receptacle. In one embodiment; the method includes forming a plurality of chambers within a fluid receptacle of the access port and covering the fluid receptacle with a septum. As mentioned, in certain embodiments, a plurality of chambers may be formed by placing an insert within the fluid receptacle of the access port so that the insert divides the fluid receptacle into different chambers that are fluidly connected to a port stem of the access port. The insert may be attached within the receptacle (e.g., by an adhesive or snap-fit connection), held in place by the septum, or otherwise secured to create the multiple chambers within the fluid receptacle of the access port. Also as mentioned, in certain embodiments, the method may include the step of inserting a base mat (e.g., a silicone base mat) into the fluid receptacle before placing the insert. In addition, a fluid-contacting surface of at least one of the chambers of the access port may be coated with a hydrophobic coating. In some variations, the step of coating a fluid-contacting surface of the fluid receptacle with a hydrophobic coating includes coating the walls of all of the chambers within the fluid receptacle with a highly hydrophobic coating, such as PTFE. In one embodiment, a method of manufacturing an implantable port includes forming a plurality of chambers within a fluid receptacle by positioning an insert therein, the insert being positioned such that each of the formed chambers is in fluid communication with a port stem, and covering the fluid receptacle with a septum such that the chambers are fluid-locked.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIGS. 7A to 7C show cross-sectional, side perspective, top, and side cross-sectional views (respectively) of one embodiment of a fluid receptacle region of a fast clear port.

FIG. 7D shows a cutaway perspective of an access port incorporating the fluid receptacle region shown in FIGS. 7A to 7C.

FIG. 8 is a side perspective view of a portion of another embodiment of a fast clear port.

DETAILED DESCRIPTION OF THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The fast clear ports described herein generally include a housing having a fluid receptacle (also referred to as a fluid reservoir), a port stem in fluid connection with the fluid receptacle, and a septum covering the fluid receptacle. In certain embodiments, the fast clear ports may include features that are believed to increase the clearance of fluid from the access port, including, for example, a base mat within the fluid receptacle, a multi-chambered configuration, a hydrophobic coating over one or more surfaces of the fluid receptacle, and combinations thereof.

Figure 1:
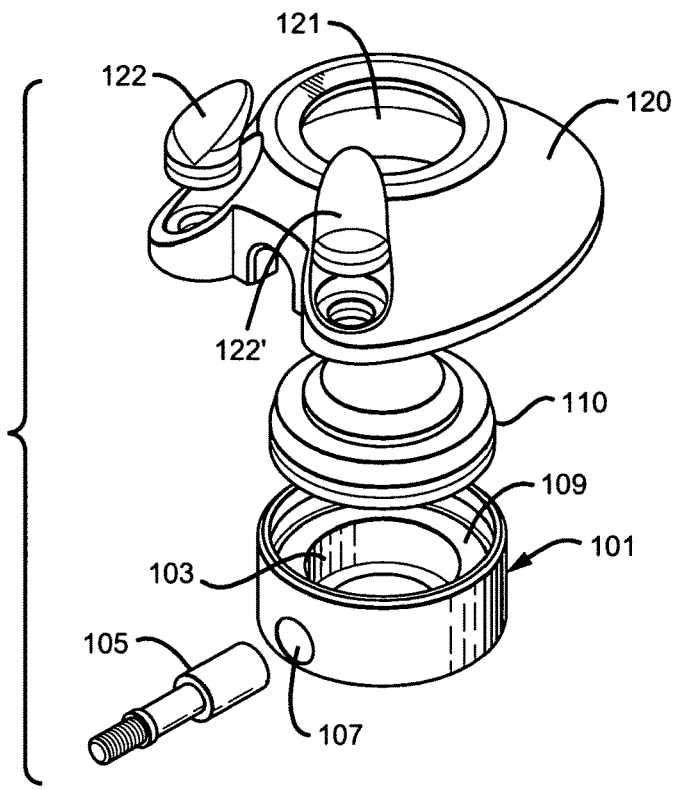
FIG. 1 is an exploded view of one example of a vascular access port.

FIG. 1 illustrates an exploded view of one example of a vascular access port. In FIG. 1, the housing 101 holds a fluid receptacle 103 that is connected to a port stem 105. Fluid within the fluid receptacle 103 can flow into or out of the port stem 105 through the connecting passage 107. The port stem 105 and the housing 101 may be fabricated separately and joined, or they may be fabricated as a single piece (e.g., by injection molding, casting, etc.). The port stem 105 may be configured to couple to a catheter. For example, the port stem 105 may be elongated and ridged or graded so that when it is inserted into the lumen of a catheter, the catheter will be secured on the port stem 105. A disc-shaped septum 110 is shown above the housing, the septum 110 being configured for placement over the fluid receptacle 103 such that a portion thereof rests on a shoulder 109 of the housing 101. The septum 110 may be made of any appropriate needle penetrable material. A cap 120 with window 121 that is open to allow a needle to access the septum 110 (and therefore the fluid receptacle 103), is configured to attach to the housing 101 and secure the septum 110 to the housing 101. The cap 120 can also include openings configured to permit insertion of suture plugs 122, 122'.

Figure 2:
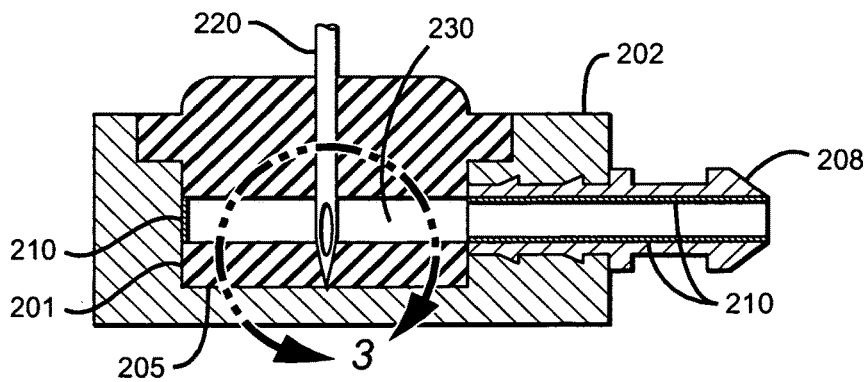
FIG. 2 is a cross-sectional view of one embodiment of a fast clear port.

A cross-sectional view of a fast clear port having a base mat is shown in FIG. 2. This access port is similar to the access port shown in FIG. 1 in certain aspects, but includes a base mat 201 disposed within the fluid receptacle of the housing 202, positioned on a bottom 205 of the fluid receptacle of the housing 202. The priming volume of the fluid receptacle is reduced by the volume of the base mat 201. As described above, the priming volume is the volume of fluid contained within the port and port stem (and may include the fluid within an attached catheter). This is also typically the volume of fluid that must be cleared to deliver fluid from a needle to the body site at the distal end of an attached catheter. The base mat may be made of any appropriate material, including a material that is hydrophobic and/or that may be repeatedly punctured by the tip of a needle inserted into the receptacle of the access port. For example, the base mat may include the same material as the septum. Examples of potential materials for the base mat include silicone (polysiloxanes), elastomeric materials, and combinations thereof.

The base mat may both reduce the priming volume of the access port, as well as assist in positioning a needle 220 that has been inserted into the access port, as shown in FIG. 2. The tip of the needle 220 may penetrate the base mat 201, allowing the opening in the needle tip to be positioned within the fluid-containing portion of the fluid receptacle 230, so that fluid may be efficiently ejected or withdrawn from the needle. Without a needle-penetrable base mat, the opening into the needle lumen has the potential to be positioned a distance (e.g., 310, FIG. 3) above the bottom 205 of the fluid-containing portion of the fluid receptacle 230. The base mat 201 allows the opening in the needle tip to be positioned closer to the bottom of the fluid-containing region, thereby eliminating the need for excess volume within the fluid receptacle, even when using standard (e.g., beveled) needles.

Figure 3:
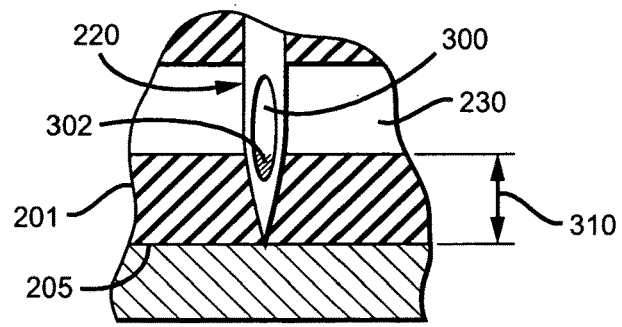
FIG. 3 is an enlarged view of a portion of the fast clear port of FIG. 2.

FIG. 3 shows a detail (from region A of FIG. 2), showing the needle 220 interacting with the base mat 201. The distal tip of the needle 220 has penetrated the base mat 201 until it contacts the bottom 205 of the fluid receptacle region of the housing 202. The housing 202 may be made of a non-penetrable material, such as, for example, a plastic material (e.g., Delrin®). In FIG. 3, the opening 300 into the lumen of the needle 220 is positioned with respect to the thickness of the base mat 201 so that the opening is substantially within the fluid-containing region of the receptacle 230. The fluid-containing region is fluidly connected to the port stem 208. In one embodiment, the thickness 310 of the base mat 201 corresponds to the distance between the needle point and the opening 300 of the needle 220 such that no portion of the opening 300 is obstructed. In another embodiment, the thickness 310 of the base mat may be chosen so that only a small portion 302 of the opening 300 of the needle 220 is obstructed by the base mat when the needle penetrates the base mat. It should be appreciated, however, that any thickness of the base mat with respect to the needle opening is contemplated herein as long as some portion of the needle opening remains unobstructed upon insertion into the fluid receptacle. A standard 19 or 22 gage needle may be used to apply or withdraw fluids from the fast clear ports, although any appropriate needle may also be used.

The fluid contacting portion of the fluid receptacle of an access port may have a hydrophobic surface which may enhance clearance of fluid from within the fluid receptacle. Clearance may be enhanced when the fluid contacting surfaces have less surface energy or affinity for injected (or withdrawn) materials. Thus, the fluid-contacting surfaces within the fluid receptacle may be lubricious (or low-friction) surfaces. Such slippery surfaces are believed to greatly reduce the frictional resistance to the passage of material. Hydrophobic surfaces may more rapidly and readily pass fluid. Hydrophobic, particularly highly hydrophobic surfaces, are believed to have a tendency to repel water because their adhesive energy and critical surface energy are very low and their contact angle is very high (the contact angle refers to the wetting contact angle of water on the surface). The surface may be hydrophobic because it is made from a hydrophobic material, or because it is coated or treated with a hydrophobic material.

Examples of appropriate hydrophobic materials that may be used include any appropriate low-friction material, such as: fluoropolymers (e.g. FEP (Fluorinated Ethylene-Propylene), PFA (perfluoroalkoxy polymer resin), PTFE (polytetrafluoroethylene), etc.), silicones, paraffins, polyethylene, etc. Super hydrophobic materials are included as hydrophobic materials. For example, polytetrafluoroethylene (PTFE) is considered a "super hydrophobic" material, and can be pre-dispersed as an ingredient in a thermoplastic compound or used as a base component in a coating formulation in order to reduce the coefficient of friction. PTFE particles embedded in a thermoplastic compound or coating material are believed to form a highly lubricious solid film over the surface. Any of the fluid-contacting surfaces within the access port (e.g., surfaces contacting the applied or withdrawn fluid) may be made of, treated with, or coated with a hydrophobic material. For example, surfaces may be made hydrophobic by modifying them using a process such as cold gas plasma, or by coating them with hydrophobic coatings.

Returning to FIG. 2, the access port shown includes a hydrophobic coating 210 on one or more of the sides of the fluid receptacle, as well as the walls of the port stem 208. In one embodiment, the port stem 208 is made of titanium or molded plastic and is coated with a material such as PTFE to provide advantages, such as, for example, improved clearance kinetics. Any of the fluid-contacting surfaces of the access port (particularly within the fluid receptacle region of the access port) may include a hydrophobic surface. For example, the fluid receptacle region may be bounded by the walls of the inner portion of the housing, the base of the inner portion of the housing, and the bottom of the septum, as shown in FIG. 1. Any (or all) of these surfaces may be hydrophobic. In addition, structures within the fluid receptacle (e.g., the walls of any insert forming the multi-chamber access ports as described below) may be hydrophobic, as well as the inner portion of the port stem and/or catheter.

In general, the access ports described herein may include any size or shape housing, fluid receptacle, and septum. Thus, although the fluid receptacles illustrated in the figures are shown as cylindrical (e.g., having a round cross-section), non-cylindrical shaped fluid receptacles (e.g., ovoid, rectangular, polygonal, etc.) may also be used. In some variations, more than one fluid receptacle may be used. The fluid receptacle may also be divided into chambers to increase priming volume as described below.

Figure 4:
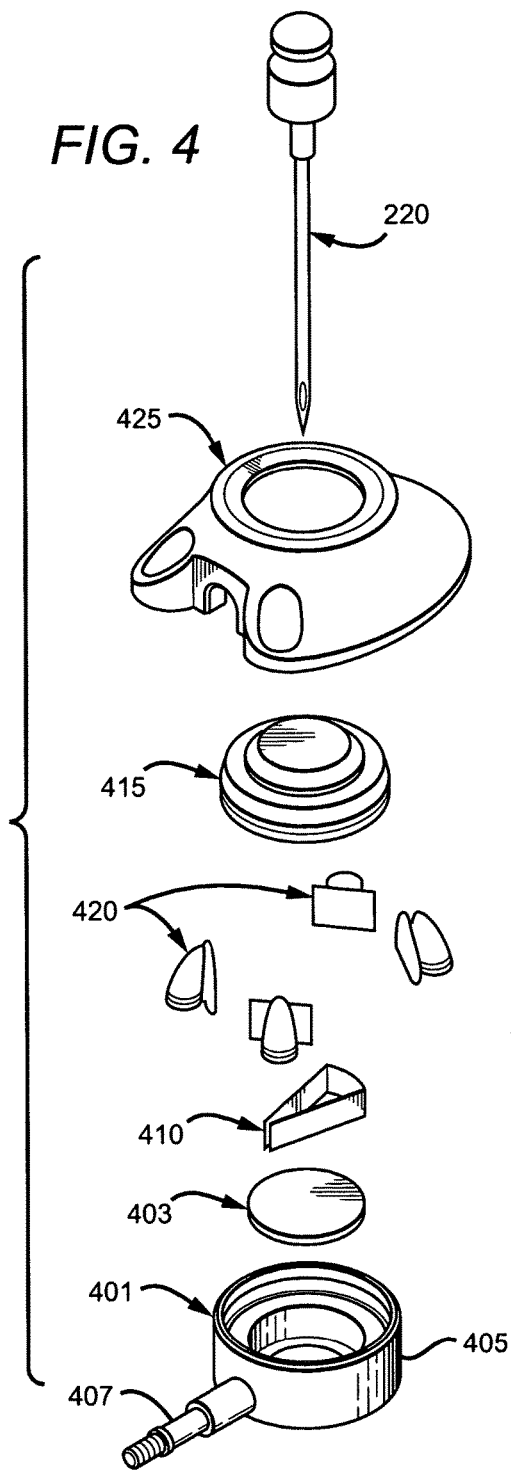
FIG. 4 is an exploded view of another embodiment of a fast clear port.

In one embodiment, the fluid receptacle of an access port may be divided into a plurality of chambers to reduce the effective volume of the fluid receptacle; the fluid receptacle may be subdivided into two or more chambers. In this embodiment each chamber has a path to a single lumen in a port stem (connecting to the catheter) so that fluid from the chambers is in fluid communication with a catheter or other conduit attached to the port stem. In certain embodiments, the multiple chambers are part of a single fluid receptacle. FIG. 4 shows an exploded view of one variation of a multi-chamber implantable vascular access port (fast clear port). The fast clear port includes a housing 401 that has an inner region forming a fluid receptacle 405. A base mat 403 may be included within the fluid receptacle, and an insert 410 divides the fluid receptacle into three equivalent chambers. The insert may include one or more opening to allow fluid to flow between the chambers of the receptacle and the port stem (and thus the catheter). A needle-penetrable septum 415 fits over the insert 410 to cover the separate chambers created in the fluid receptacle 405. Four suture plugs 420 may also be included, as well as a cap 425 to secure the edge of the septum 415 against the housing 401. A port stem 407 is shown connected to the housing 401.

A multi-chamber access port may be manufactured by assembling the parts shown schematically in FIG. 4. For example, a method of manufacturing an implantable vascular access port having a divided fluid receptacle may include forming a plurality of chambers within a fluid receptacle of the access port by placing an insert 410 within the fluid receptacle 405 of the access port so that the insert 410 divides the fluid receptacle into different chambers that are fluidly connected to a port stem 407 of the access port. Although FIG. 4 shows a multi-chamber fast clear port that includes a base mat within the fluid receptacle of the access port, certain embodiments do not include a base mat 403. For example, in some variations, the insert 410 is positioned directly against the base of the inner portion of the housing forming the fluid receptacle 405. Moreover, as explained above, any of the fluid-contacting surfaces of the chambers the fluid receptacle may be hydrophobic. In some variations, the surfaces are coated with a hydrophobic material (e.g., PTFE).

Figure 5:
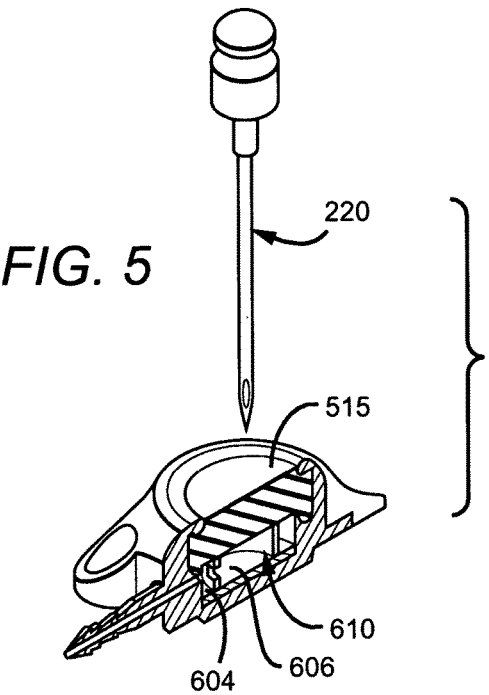
FIG. 5 is a perspective cutaway view of another embodiment of a fast clear port.
Figure 6:
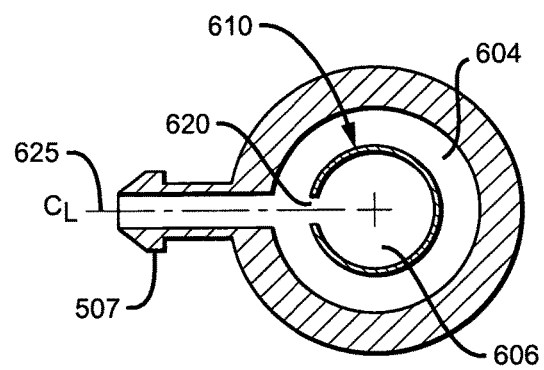
FIG. 6 is a cross-sectional view of the fast clear port of FIG. 5.

The multi-chamber access ports described herein may include two or more chambers, which may be configured in a variety of shapes and sizes. FIGS. 5 and 6 illustrate another variation of a multi-chamber access port. In the cutaway view shown in FIG. 5, a fluid receptacle has been divided into two chambers, an outer chamber and an inner chamber. The outer chamber 604 of the fluid receptacle and the inner chamber 606 of the fluid receptacle are formed by a circular insert 610. When a needle 220 is inserted through the septum 515 of the access port, it can enter either the inner chamber 606 or the outer chamber 604 of the fluid receptacle, depending on where the needle is inserted through the septum 515. In one embodiment, the inner chamber 606 and outer chamber 604 of the fluid receptacle hold a substantially equivalent volume of fluid. FIG. 6 shows a cross-section through the fluid receptacle of the access port shown in FIG. 5. The insert 610 can be seen as circular, having an opening 620 positioned in fluid communication with the port stem 507. The opening 620 is a fluid exit (or entrance) site through which fluid flows from the inner chamber 606 into the port stem, passing through a region of the outer chamber 604.

In general, the different chambers of the fluid receptacle may be fluid-locked, meaning that when fluid is added or taken from one chamber, it does not substantially get taken (or added) from the other chambers of the fluid receptacle. Fluid-locking may be a result of the configuration of the fluid pathways into and out of the different chambers. For example, the inner and outer chambers 606, 604 shown in FIG. 6 are fluid locked because an increase or decrease in fluid pressure in one chamber does not result in a substantial fluid differential in the other channel, and thus there is not a substantial flow into or out of the other channel. Because the exit (or entrance) from the inner 606 chamber is aligned with the port stem pathway exiting the access port into a large (possibly variable) volume, fluid inserted into the inner chamber 606 will exit the access port without substantially entering the outer 604 chamber. Similarly, fluid inserted into the outer 604 chamber will exit the access port without substantially entering the inner 606 chamber. In general, a vessel including a plurality of fluid-locked chambers will not have different pressures in the other chamber(s) when the fluid pressure changes in one chamber. Although some fluid may be exchanged between the chambers (e.g., by diffusion or turbulence), the majority of fluid will be exchanged between the chamber into which the needle is inserted, the port stem and catheter or fluid conduit attached thereto. In FIG. 6, the different chambers are connected by an opening 620 in the insert 610. This opening 620 is oriented on the centerline of the inner diameter of the port stem 625. As mentioned above, the different chambers may define equivalent volumes or fluid pathways. For example, the insert shown in FIG. 6 divides the fluid receptacle into multiple chambers that hold approximately the same amount of fluid. Thus, fluid injected into any of these chambers may clear at approximately the same rate.

In operation, a needle 220 is inserted through the septum 515 of a multi-chamber fast clear access port and a single chamber is accessed for infusion of fluid. Since the barriers forming the separate chambers are relatively thin, it is believed to be unlikely that they will interfere with the insertion of the needle. However, in some variations, the top of the barriers (e.g., inserts) may be rounded or beveled to help deflect the tip of the needle so that the needle inserts into one chamber or another. Further, the barriers (e.g., formed by an insert) may be made of a needle-impenetrable material. When the port and catheter are primed with fluid (e.g., when any air is evacuated), needle will inject or aspirate from the access port by exchanging the volume of the chamber in which the needle was inserted. Because the different chambers are fluid-locked, the transport between chambers is minimized and the majority of fluid is exchanged between the chamber into which the needle inserted and the larger volume represented by the open catheter connection to the port stem. Because of the lack of differential pressure, flow from (or into) other chambers (other than the one in which the needle is inserted) arises mostly from diffusion and small eddy currents.

The fluid receptacle may be divided into multiple chambers by any appropriate structure, including the inserts described above (and shown in the figures), as well as by barriers that are formed integrally with the housing. For example, the housing may be formed of a plastic material that is molded, extruded, etc., and the barriers between the chambers are formed with the rest of the housing. In some variations, an insert may be removable or formed separately and attached to the housing. Furthermore, the insert(s) forming the different chambers may be any appropriate shape, including rounded (e.g., oval, circular, etc.), or liner. An insert may be a single piece or multiple pieces. For example, the insert may be a thin flat strip of material that has been bent or formed into a particular configuration or shape. A flat region of the insert may form walls (barriers) between the different chambers. The insert may be secured within the fluid receptacle by any appropriate means. For example, the insert may be compressed between the base of the inner portion of the housing and the septum (particularly when an elastomeric base mat is used), or the insert may be attached within the fluid receptacle through the use of an adhesive, solvent, weld, and/or other attachment methods known to one skilled in the art.

FIGS. 7A-D show another variation of a region of the housing of a multi-chamber fast clear access port. FIG. 7A shows a section through the housing of an access port having a pie-shaped insert that divides the fluid receptacle 710 into three approximately equivalent, fluid-locked regions (v1, v2, v3). One side of the insert 701 is affixed to a wall of the inner region of the housing (e.g., by a silicone seal). The opposing side of the insert includes an opening so that fluid within v2 may exit into or enter from the port stem when differential pressure is applied within a chamber. The insert 701 is positioned within the fluid receptacle such that sides 703 and 705 do not contact the walls of the fluid receptacle, permitting fluid to flow between v1 and the port stem and v3 and the port stem. A perspective view of this housing region is shown in FIG. 7B. The walls of the insert 701 project up from a base of the fluid receptacle 710, so that the bottom of the septum (not shown) can completely seal off the chamber formed by the insert when the septum is attached to the housing region. In general, the chambers v1, v2, v3 may be sealed except for the opening fluidly connecting them with the port stem and catheter or fluid conduit attached thereto. FIG. 7C shows a top view of this same region of the housing. FIG. 7D shows a perspective cut-away view of a fast clear port 720 incorporating the housing region and insert 710 described in FIGS. 7A-7C, in which the septum has been removed to show the divided fluid receptacle region of the housing. In addition to the insert 701, fast clear port 720 includes a base mat 706.

FIG. 8 illustrates a dual-chamber fast clear port 810, showing a portion of a housing including insert 801 that divides a fluid receptacle into two approximately equivalent chambers. The insert 801 is positioned such that a fluid pathway is provided between each created chamber and the port stem (not shown).

Figure 9:
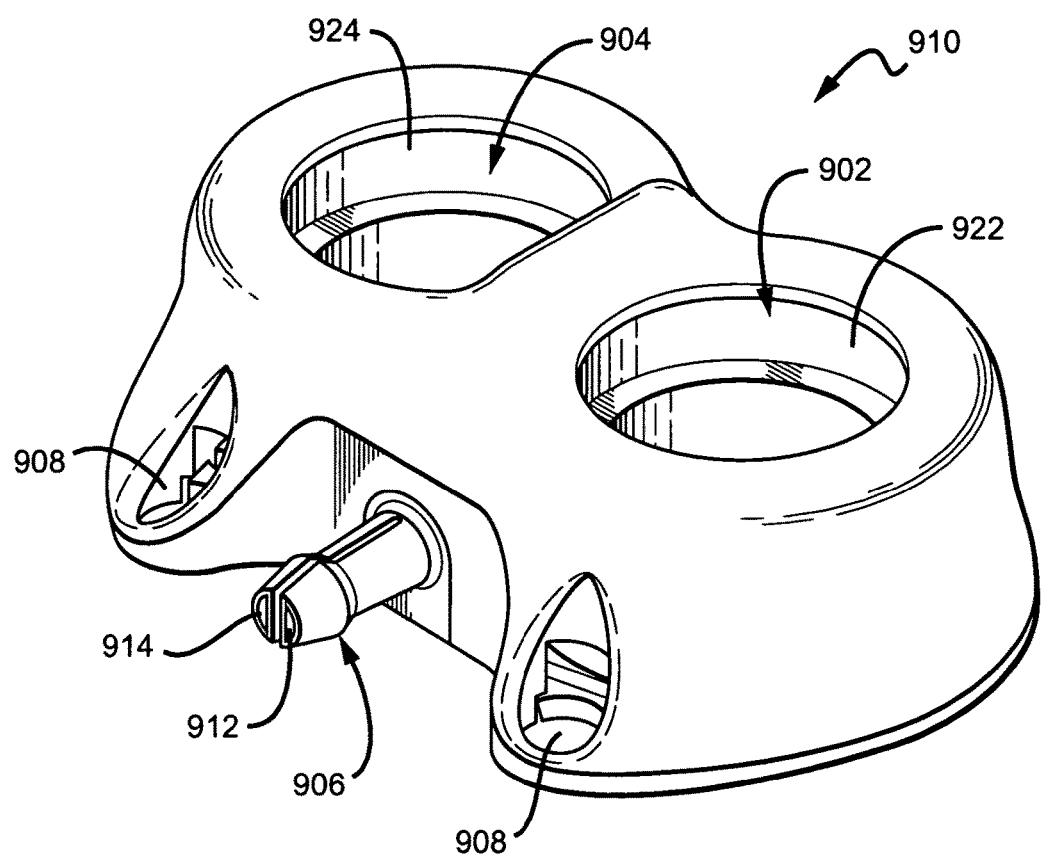
FIG. 9 is a side perspective view of another embodiment of a fast clear port.

In one embodiment, a fast clear port includes more than one fluid receptacle (e.g., two, three, etc.), each fluid receptacle having two or more chambers formed by an insert. As discussed above, the insert may be separate from the fluid receptacle and secured therein during manufacturing, or the insert may be an integral portion of the fluid receptacle (e.g., molded into the fluid receptacle). In one variation of this embodiment, a single port stem is connected to the multiple fluid receptacles via separate passageways. Thus, for example, in an embodiment including two fluid receptacles, the port stem would be divided along its length into two separate passageways, each of which is respectively fluidly connected to a fluid receptacle with multiple chambers. One example of this embodiment is shown in FIG. 9, in which fast clear port 910 includes a first fluid receptacle 902 and a second fluid receptacle 904. A port stem 906 has a first passageway 912 fluidly connected to fluid receptacle 902 and a second passageway 914 connected to fluid receptacle 904. Although not shown, in this embodiment a first and second septum cover the first and second fluid receptacles respectively, extending through openings 922 and 924, and suture plugs are fashioned to be inserted within the cap openings 908. In such an embodiment, a dual lumen catheter (not shown) with separate lumens could be attached to the port stem such that the fluid contained within each fluid receptacle remains separated throughout a length of the catheter. As stated, each fluid receptacle of a fast clear port with more than one fluid receptacle may contain two or more chambers formed by an insert. The multiple chambers of each fluid receptacle, in one embodiment, are in fluid communication with the same passageway of the port stem and respective lumen of the catheter.

In another variation of this embodiment, each fluid receptacle is connected to a different port stem, each of which is connected to a separate single lumen catheter. As described above, each of the chambers of the fluid receptacles in a fast clear port including more than one fluid receptacle could be fluid-locked. Moreover, each of the fluid receptacles, or individual chambers thereof, could contain one or more base mat. Further, surfaces of one or more of the chambers could be coated with a hydrophobic material.

As mentioned, certain embodiments of the multi-chamber fast clear ports described herein may be used in combination with one or more base mats. For example, an insert may be applied between a base mat and a septum. In some variations, multiple base mats may fit into each chamber. Furthermore, any of the fluid-contacting surfaces of the fluid receptacle (e.g., the barriers or walls forming the separate chambers) may be hydrophobic. In some variations, all of the fluid contacting surfaces within the fluid receptacle are hydrophobic. A vascular access system may include any of the fast clear ports described herein (or any combination of these ports). In addition, a vascular access system may include a catheter configured to be implanted within a subject so that the distal end of the catheter is adjacent to a target site, and the proximal end of the catheter is configured to attach to the port stem of a fast clear port. Systems may also include a needle or needles for accessing the fast clear port. A fast clear port or system may also be included as part of a kit. Kits may include instructions (in any man or machine-readable format), and may be packaged and/or sterilized for medical use.

As described above, a fast clear port may be implanted into any appropriate region of subject, particularly a subject in need thereof. (As used herein "subject" may include any appropriate subject, including non-human subjects). A method of implanting the fast clear port includes implanting a catheter so that the distal end of the catheter is positioned adjacent to a target site after the port has been implanted, attaching the proximal end of the catheter to the port stem of an access port, and implanting any variation of the fast clear ports described herein. Once the fast clear port has been implanted, it may be used by inserting a needle (e.g., a 19 or 21 gauge needle) through the septum and into a fluid receptacle region of the access port. The needle may be inserted until the needle tip opening is positioned in the fluid-containing region of the housing. In some variations, this means that the tip of the needle penetrates the base mat until the tip contacts the non-penetrable base of the housing. Fluid may then be injected into (or withdrawn from) the fluid receptacle of the access port. In some variations, the needle is inserted through the septum into one of a plurality of component chambers that makeup the fluid receptacle. After inserting or removing fluid, the needle can be withdrawn. Thus, the access port can be used repeatedly.

It is noted that, as used in this specification and the appended claims, the singular forms "a," "an" and "the" include plural referents unless the context clearly dictates otherwise. Thus, for example, the term "a port" is intended to mean a single port or a combination of ports, "a fluid" is intended to mean one or more fluids, or a mixture thereof. In addition, it is to be understood, that unless otherwise indicated, this invention need not be limited to applications in human. As one of ordinary skill in the art would appreciate, variations of the invention may be applied to other mammals as well. Moreover, it should be understood that embodiments of the present invention may be applied in combination with various catheters, drug pumps, and infusion devices.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed as new and desired to be protected by Letters Patent of the United States is:

1. An implantable port, comprising:
    a housing including a fluid receptacle divided into two or more chambers;
    a port stem including a single lumen in fluid communication with the two or more chambers, the port stem designed for coupling to a catheter via insertion of the port stem into a lumen of the catheter; and
    a septum covering the fluid receptacle configured to allow a needle to be inserted therethrough and enter into either of the two or more chambers.

2. The implantable port according to claim 1, further comprising an opening between the two or more chambers to allow fluid to flow between the port stem and the two or more chambers of the fluid receptacle.

3. The implantable port according to claim 1, wherein the two or more chambers are fluid-locked.

4. The implantable port according to claim 3, wherein the two or more chambers, which are fluid-locked chambers, are formed by at least one insert.

5. The implantable port according to claim 1, wherein the two or more chambers comprise an inner chamber and an outer chamber, the outer chamber surrounding the inner chamber.

6. The implantable port according to claim 1, wherein the fluid receptacle includes a pie-shaped insert dividing the two or more chambers of the fluid receptacle into three chambers.

7. The implantable port according to claim 1, further comprising a base mat disposed within the fluid receptacle.

8. The implantable port according to claim 7, wherein the base mat comprises a penetrable material.

9. The implantable port according to claim 1, wherein a fluid contacting portion of the fluid receptacle comprises a hydrophobic surface.

10. The implantable port according to claim 1, wherein all fluid-contacting surfaces of the two or more chambers comprise a hydrophobic coating.

11. The implantable port according to claim 10, wherein the hydrophobic coating comprises polytetrafluoroethylene.

12. An implantable port, comprising:
    a housing including a fluid receptacle divided into an inner chamber and an outer chamber circumscribing the inner chamber;
    a port stem including a single passageway in fluid communication with the inner chamber and the outer chamber, the port stem designed for coupling to a catheter via insertion of the port stem into a lumen of the catheter; and a septum configured to cover the fluid receptacle and configured to allow a needle to be inserted therethrough and enter into either of the inner chamber or the outer chamber.

13. The implantable port according to claim 12, wherein the inner chamber and the outer chamber are formed by a circular insert separating the inner chamber from the outer chamber.

14. The implantable port according to claim 13, further comprising an opening in the circular insert providing fluid communication between the port stem, the outer chamber, and the inner chamber, the opening positioned to maintain a portion of the circular insert between the inner chamber and the outer chamber.

15. The implantable port according to claim 12, wherein the inner chamber and the outer chamber are separated by a barrier, the barrier including an opening aligned with the port stem to provide fluid communication between the port stem, the inner chamber, and the outer chamber.

16. The implantable port according to claim 15, wherein a portion of the barrier completely circumferentially surrounds the inner chamber, such that the opening in the barrier creates a raised portion between the port stem and the inner chamber.

17. The implantable port according to claim 12, wherein the inner chamber and the outer chamber are fluid-locked such that fluid introduced into a first chamber does not substantially enter another chamber.

* * * * *